United States Patent [19]

Thiruvengadam et al.

[11] 4,231,259

[45] Nov. 4, 1980

[54] METHOD AND APPARATUS FOR NON-DESTRUCTIVE EVALUATION UTILIZING THE INTERNAL FRICTION DAMPING (IFD) TECHNIQUE

[76] Inventors: Alagu P. Thiruvengadam, 10509 William Tell La., Columbia, Md. 21044; Ambrose A. Hochrein, Jr., 18521 Kilt Ter., Olney, Md. 20832

[21] Appl. No.: 933,114

[22] Filed: Aug. 11, 1978

[51] Int. Cl.³ ............................................. G01N 29/00
[52] U.S. Cl. ......................................... 73/584; 73/588
[58] Field of Search ................. 73/579, 582, 584, 588, 73/594

[56] References Cited

U.S. PATENT DOCUMENTS

| | | | |
|---|---|---|---|
| 3,345,861 | 10/1967 | Heath | 73/584 |
| 3,453,872 | 7/1969 | Botsco | 73/588 |
| 3,564,903 | 2/1971 | Woodmansee et al | 73/588 |
| 3,592,050 | 7/1971 | Nutt et al. | 73/588 |
| 3,623,358 | 11/1971 | Sugimoto | 73/588 |
| 4,128,011 | 12/1978 | Savage | 73/594 |

*Primary Examiner*—Stephen A. Kreitman
*Attorney, Agent, or Firm*—Burns, Doane, Swecker & Mathis

[57] ABSTRACT

A non-destructive evaluation technique particularly suited for in situ testing utilizes significant changes in internal friction damping (IFD) as an indicating factor. A baseline for the specific damping capacity of an object is determined and a tolerance range is established from the baseline. Measurements of the specific damping capacity are periodically made and checked to see if they are within the tolerance range. Unexpected changes in specific damping capacity indicate the presence of an incipient flaw in the object. The evaluation technique can also be used to locate flaws, monitor crack growth and predict useful life. Apparatus for measuring specific damping capacity is also disclosed.

23 Claims, 6 Drawing Figures

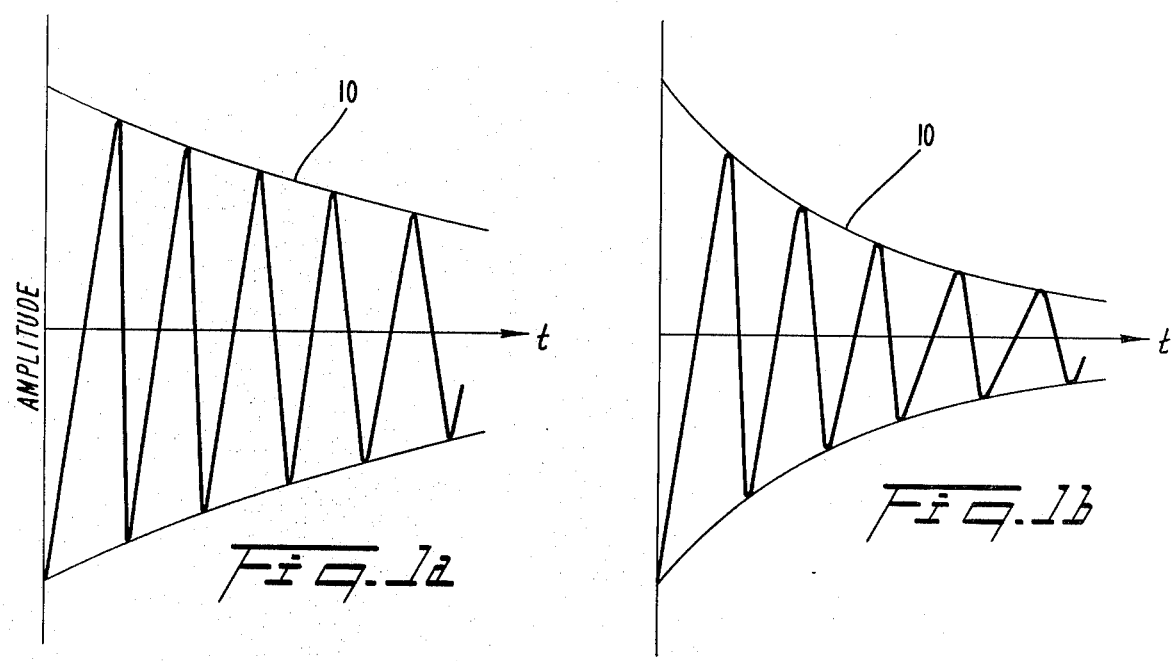
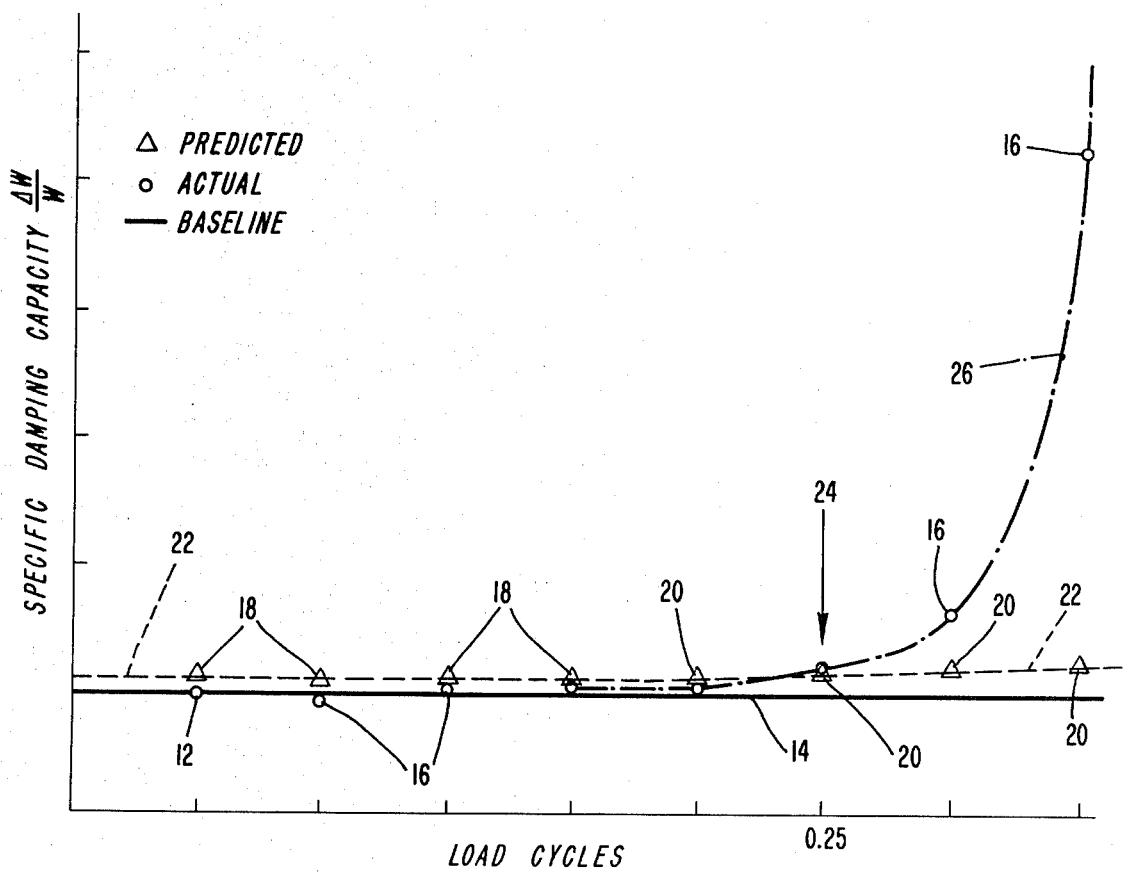

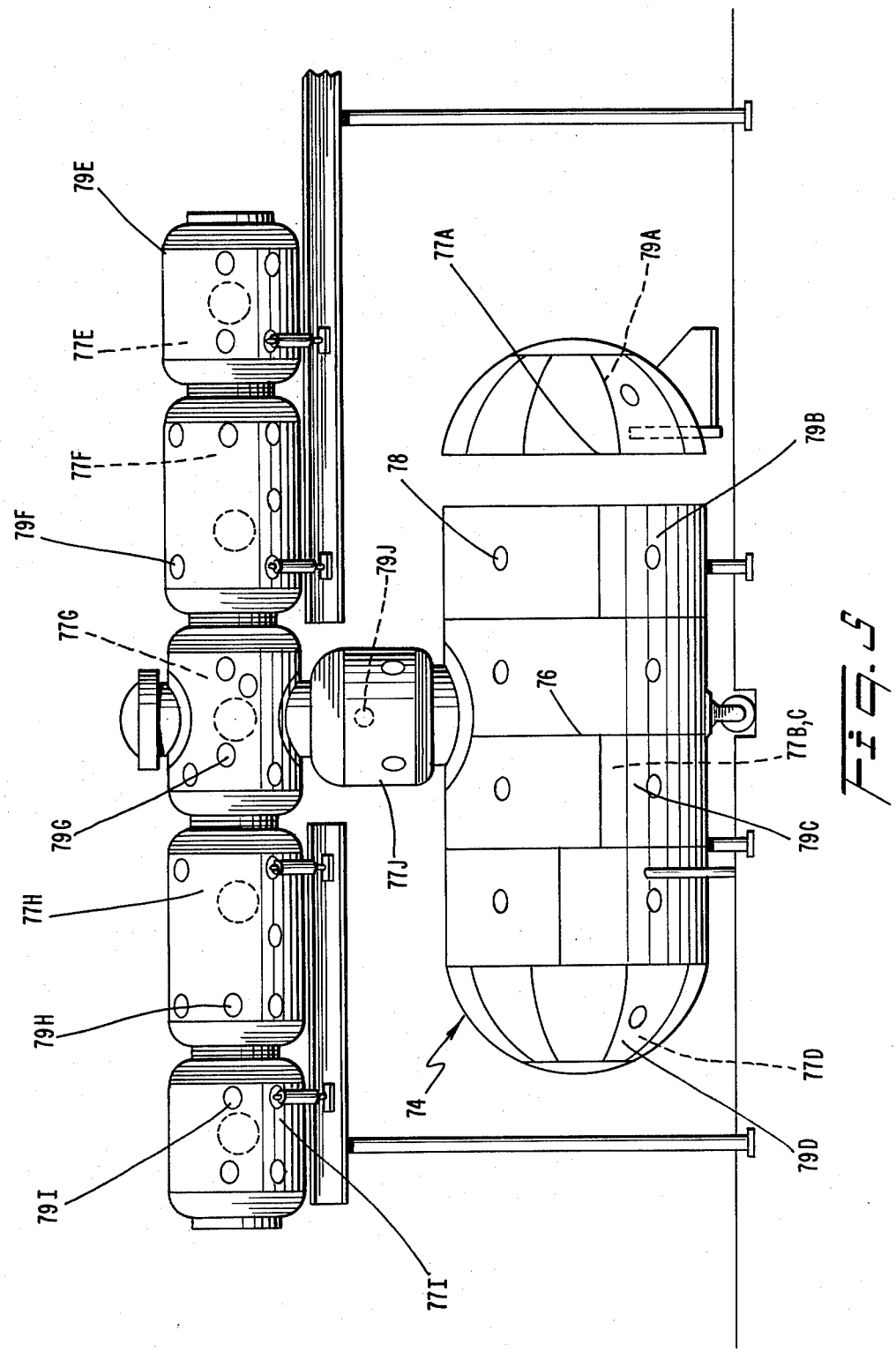

METHOD AND APPARATUS FOR NON-DESTRUCTIVE EVALUATION UTILIZING THE INTERNAL FRICTION DAMPING (IFD) TECHNIQUE

BACKGROUND OF THE INVENTION

The present invention relates to the non-destructive evaluation of the condition of a material, and more particularly to in situ non-destructive evaluation which is capable of determining the condition of a material by measuring its specific damping capacity, or internal friction damping (IFD).

Knowledge of the specific damping capacity of a material has a variety of applications. For example, it is used to determine the authenticity of coins, the soundness of castings, the operating condition of railroad wheels and the quality of musical instruments and glassware. Furthermore, it is useful as a research tool in physical metallurgy, vibration control of high-speed vehicles, metal fatigue and the study of properties of metals and alloys. The present invention is particularly concerned with, but not limited to, the utilization of the specific damping capacity of a material as a means of detecting and monitoring flaws in objects and predicting their useful life.

In the past, the specific damping capacity of a material has been determined by freely suspending an object, vibrating the object at its resonant frequency, and measuring the amplitude of the vibrations. This technique is disclosed in U.S. Pat. Nos. 3,592,050, issued to Nutt, Jr., et al on July 13, 1971, and 3,623,358, issued to Sugimoto on Nov. 30, 1971.

As is well known, when an object is vibrated at its resonant frequency, the amplitude of the vibrations is at a maximum with respect to vibration at any other frequency for a given vibration inducing input force. This can result in relatively high amplitude vibrations which produce high level stresses on the object being evaluated. Since the stress vs. strain curve for a material is normally not linear throughout the stress range, high level stress imparted to an object produces an output signal which is not always linearly proportional to the input force.

In the prior art systems such as those disclosed in the previously mentioned patents, the object being tested is freely suspended by hanging the object with the use of wires or the like or by placing the object on a support which acts as a fulcrum, so that the object is free to vibrate at its resonant frequency. This technique is not practical for the evaluation of structural components located in situ. For example, where a boiler tank is to be tested for its structural soundness after a period of use, it is necessary to disconnect the tank from the remainder of the system into which it is incorporated, remove it from its support and suspend it so that it can freely vibrate. This means that the system must be shut down while the test is being performed, resulting in lost time and probably economic loss.

Furthermore, where an object is suspended and vibrated, it is only possible to test the structural integrity or composition of the object as a whole. It is not possible to individually test non-separable portions of the object or to determine the location of detected flaws with a resonable degree of precision.

In the prior art non-destructive evaluation systems, the results of the measurements obtained during testing were used only to determine the material composition or structural condition of the tested object. They were not utilized to obtain other useful information such as the life expectancy of an object or to monitor conditions of the object such as crack growth rate.

OBJECTS AND SUMMARY OF THE INVENTION

Accordingly, it is an object of the present invention to provide a novel method and apparatus for nondestructive evaluation which does not necessarily require vibration of a tested object at the object's resonant frequency.

It is another object of the present invention to provide a novel method and apparatus for non-destructive evaluation which operates in the linear response range of a tested object.

It is a further object of the present invention to provide a novel method and apparatus for non-destructive evaluation which does not require the tested object to be freely suspended and hence is suitable for in situ testing.

It is yet another object of the present invention to provide a novel method and apparatus for non-destructive evaluation which enables individual portions of a unitary object to be tested for characteristics of interest.

It is yet a further object of the invention to provide a novel method and apparatus for non-destructive evaluation which permits the location of a flaw within an object to be determined with a reasonable degree of accuracy.

It is still another object of the present invention to provide a novel method and apparatus for non-destructive evaluation which enables incipient flaws and the useful life expectancy of an object to be predicted and permits continuous monitoring of the conditions of the object.

These and other objects are achieved in accordance with the present invention by imparting an excitation to an object to be tested which produces a stress in the anelastic stress range of the object. As used in the context of the specification and the claims, the term "object" defines a variety of different items which can be subjected to non-destructive evaluation. It is not limited to a unitary item which is made up of a single composition of material, but may include structures such as pressure hulls, drilling platforms or pipelines which include a number of different components of different composition which are welded or otherwise joined together.

The imparted excitation is preferably induced by applying a series of pulses to the object at a frequency other than the resonant frequency of the object. The energy level of the excitation decays within the object due to the internal friction or specific damping capacity of the object. The percentage of energy decay is measured and recorded at periodic intervals. The recorded values are used to determine a baseline for the specific damping capacity of the object, from which the expected values of future measurements are established.

Subsequent measurements are compared with the expected values to determine, among other things, when an incipient flaw is present in the object, crack growth rate or the useful life expectancy of the object.

In a further preferred embodiment of the invention, the decay of the energy level of the excitation is measured at a plurality of points on the object to determine the location of any detected flaws in the object.

BRIEF DESCRIPTION OF THE DRAWINGS

FIGS. 1a and 1b are graphs illustrating the output signal obtained when an excitation is induced in a good object and an object having a flaw therein, respectively;

FIG. 2 is a graph illustrating the manner in which the specific damping capacity is recorded and used to detect incipient flaws and predict useful life of an object;

FIG. 5 is a view in elevation depicting the location of input and output signals for measuring the specific damping capacity of an in situ object.

DETAILED DESCRIPTION OF THE PREFERRED EMBODIMENTS

Figure 3:
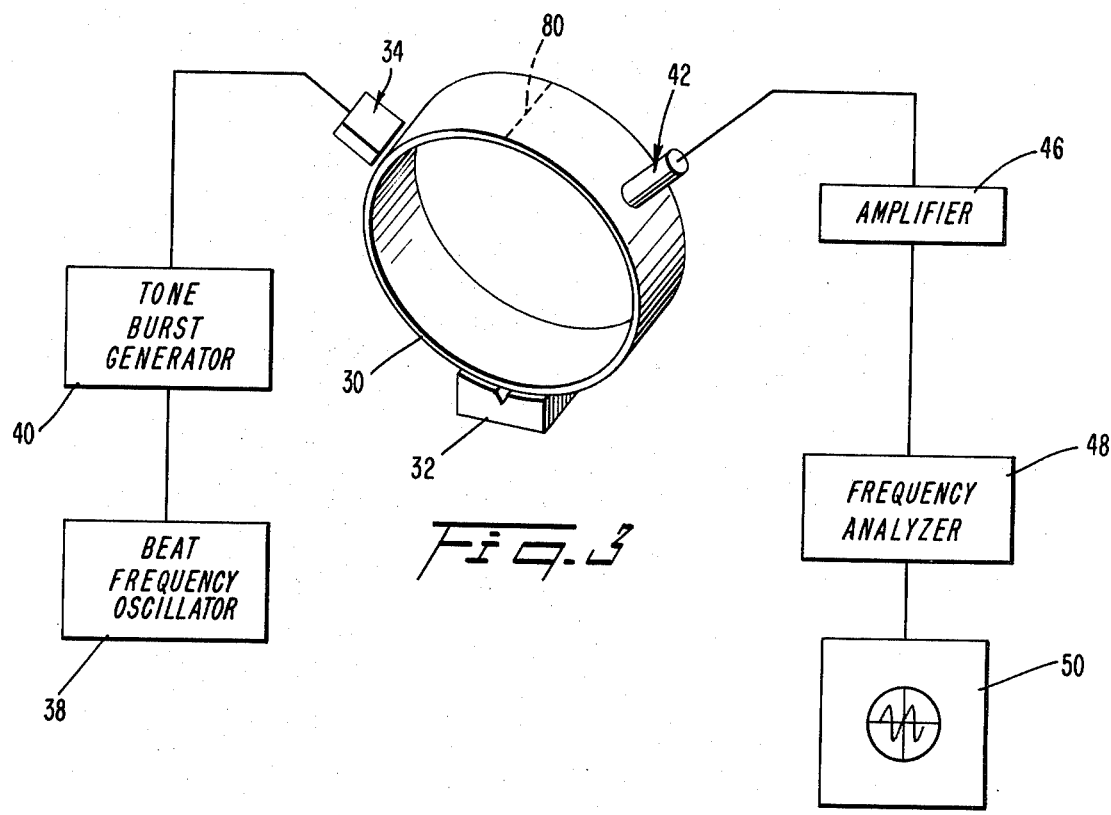
FIG. 3 is a schematic block diagram of apparatus for measuring the specific damping capacity of an object.

The specific damping capacity of an object is due to the object's deviation from perfect elastic behavior. This deviation occurs even at small stress levels and is sometimes referred to as the anelasticity of the material contained in the object. Specific damping capacity D, is defined as:

$$D = \Delta w/w$$

where:

$\Delta w$ is the amount of energy dissipated in one cycle of vibration of an object, and w is the total energy of the cycle.

The dissipation of energy is caused by a number of different factors which are well known to those familiar with the properties of materials.

The effect of the specific damping capacity with respect to different conditions of a material is illustrated in FIGS. 1a and 1b. When an object is struck, or an excitation is otherwise imparted thereto, the object will vibrate and the amplitudes of the vibrations decrease with time. If an object made of material having no flaws is struck, the rate of decrease of the vibration amplitudes is relatively small, as seen in FIG. 1a. If, however, a flaw such as an incipient crack is present in the object, relatively large amounts of energy are dissipated during each cycle of vibration, as shown in FIG. 1b.

The slope of the line 10, which defines the envelope of the amplitude of the vibrations with respect to time, is determinative of the specific damping capacity of the object. The techniques for determining the slope of the line and the specific damping capacity from the amplitude of the vibrations will be obvious to those of ordinary skill in the art. Since the line 10 is asymptotic with respect to the center line (Amplitude=0) and has an exponential characteristic, it is preferable that the slope of the line defining the envelope for the natural logarithm of amplitude with respect to time be used since it is more nearly linear.

As can be seen, the specific damping capacity of an object having a flaw therein is greater than that of a flawless object. The present invention utilizes this phenomenon as a means for detecting flaws in objects and for predicting the useful life of the object. More specifically, any changes in the specific damping capacity which are greater than an expected deviation will indicate that an incipient flaw is present in the object. The rate at which the change in specific damping capacity occurs can be used to monitor crack growth rates and to predict the useful life of the object.

The manner in which the specific damping capacity is used as a detection and prediction tool is illustrated in FIG. 2. The specific damping capacity of an object of interest is measured and recorded at periodic intervals. As illustrated, the measurements are made after a predetermined number of cycles of load in the operation of the object. For example, measurements can be made after each 10,000 load cycles. The periodic intervals may also be determined with respect to time rather than load cycles.

After the first two or three measurements 12, 16 of the specific damping capacity are made and recorded, a baseline 14 for the specific damping capacity of the object is statistically determined from these measurements. Subsequent measurements 16 made during the early life of the object are used to verify the baseline or adjust it as necessary. The baseline 14 is preferably not determined until two or three periodic measurements have been made and recorded. This enables the initial determination of the baseline to be made with a higher degree of accuracy.

Once the baseline 14 has been determined, a set of limit values 18, 20 are established. These values indicate the expected relationship of the measured values 12, 16 to the baseline 14. More specifically, the established limit values 18, 20 define an acceptable degree of tolerance between the measured values 12, 16 and the baseline 14, i.e., the maximum expected measured value for an object without cracks or other flaws.

The predicted limits 18 in the early life of the object define a set of points 22 which are substantially parallel to the baseline 14. The limits 18 are established by determining a maximum acceptable tolerance for deviation of the measured value from the baseline. The predicted values 20 for the later life of the object successively deviate from the baseline 14 by greater amounts. The amount of change between successive values is determined from a knowledge of the characteristics of the object in general, such as expected life of a good object and change in specific damping capacity over its expected life.

After the baseline 14 and the predicted values 18, 20 are established, subsequent measured values are monitored to observe their relationship to the predicted values 18, 20. As long as the measured values are less than or equal to the predicted values 18, 20, the object has not developed any incipient flaws, at least within the predetermined tolerance range.

If, however, two consecutive measured values are greater in magnitude than their associated predicted values, it is highly probable that the specific damping capacity has changed significantly. From this change, a prediction of incipient failure can be ascertained. Detection of such a condition is illustrated in FIG. 2 as indicated by the arrow 24.

Measurements made subsequent to the detection 24 of a flaw in the object can be used to monitor the growth rate of a crack or other faulty condition caused by the flaw. The rate of change between successive measurements, determined from a line 26 interconnecting the measurements, can be used to predict the remaining useful life of the object. By knowing the rate of change of the specific damping capacity, it will be possible to predict when the specific damping capacity will reach a predetermined threshold level which is indicative of a flaw rendering the object no longer useful.

One example of such a flaw is a crack in the wall of a boiler tank, which crack permits water to seep from the tank. The specific damping capacity of a tank having such a crack can be determined beforehand, and from this it will be possible to predict when a tank being tested will reach such a condition.

One example of apparatus which can be used to measure the specific damping capacity of an object is illustrated in FIG. 3. The object being tested is illustrated as a metal ring 30. The ring 30 is supported by a suitable support mechanism 32. While illustrated here as a single component isolated from the system in which it is to be used, it is to be understood that the disclosed embodiment of the measuring apparatus is also applicable to multi-component structures, and to objects located in situ.

Excitations are induced in the tested object 30 by means of an exciter 34. A number of different types of exciters can be used to induce excitations in the object. The exciter 34 can be a magnetic device which is physically connected to the object 30. An input signal to the magnetic device causes the device 34 to shake the object in an oscillatory motion and induce excitations therein.

Alternatively, the magnetic device can be located in close proximity to the object 30 but not connected thereto. When the magnetic device, e.g., a solenoid, is actuated, it moves into and out of contact with the tested object 30, rapping against the object and inducing excitations therein.

In a third embodiment of a magnetic exciter device 34, the device need not come into contact with the tested object 30. In this embodiment, the tested object 30 is magnetically sensitive. The exciter 34 sets up a varying magnetic field which attracts and repels the tested object. The force on the object causes the excitations to be induced therein.

Figure 4:
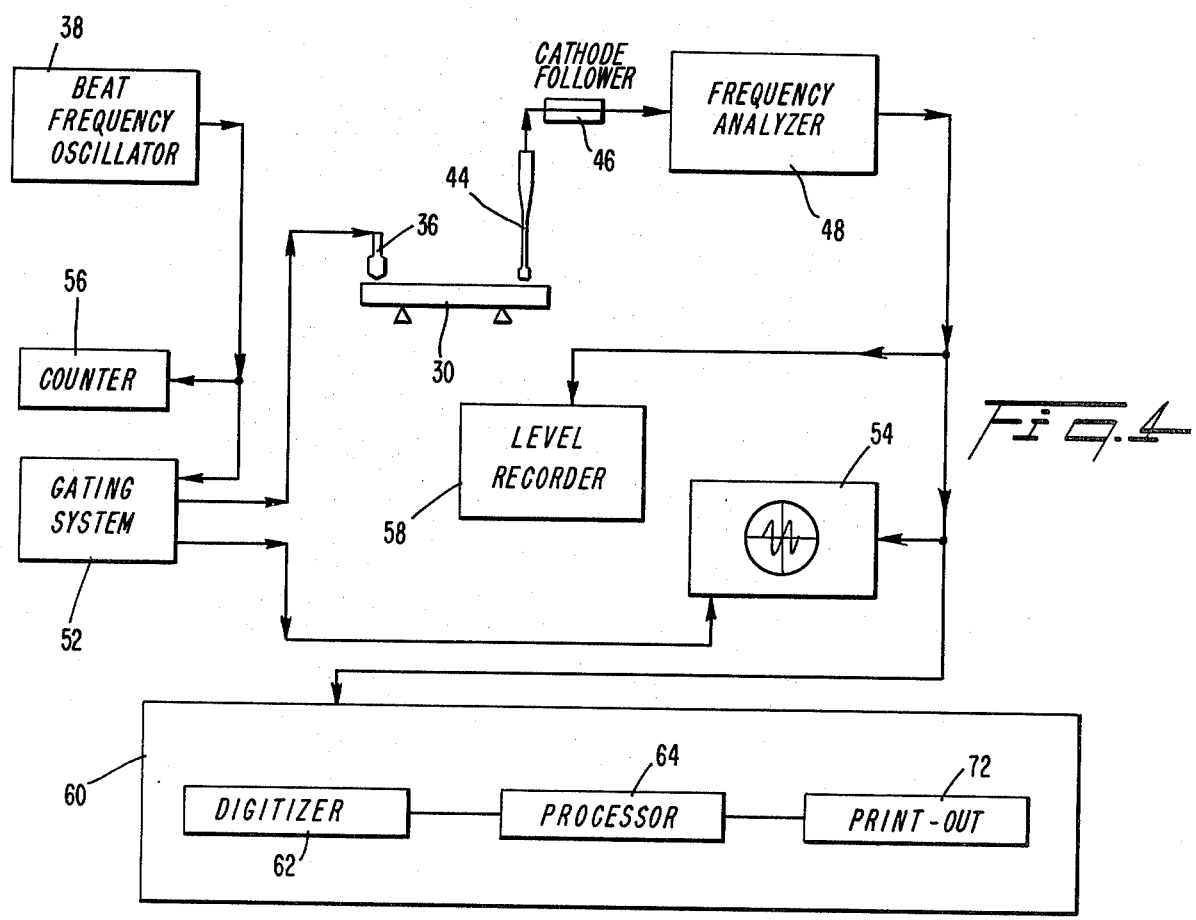
FIG. 4 is a schematic block diagram of a second embodiment for measuring specific damping capacity.

In addition to magnetic devices, the excitations can be induced in the tested object 30 by other known means. For example, the exciter can be an acoustic transmitter 36 (FIG. 4). The acoustic transmitter 36 is located in close proximity to the tested object 30 and induces excitations comprising vibrations in the audio frequency range.

The exciter 34 can also be a mechanical striker which is electrically or mechanically operated. The striker raps against the object to impart excitations in the form of vibrations. Furthermore, the exciter 34 can be a hammer which is manually actuated.

From the foregoing, it will be obvious to those skilled in the art that numerous other forms of exciters which impart a detachable excitation in the tested object 30 can be used in the context of the present invention.

To actuate an electrically operated exciter 34, a beat frequency oscillator 38 produces an electrical signal having a predetermined period. The output signal of the beat frequency oscillator is gated by a tone burst generator 40 and then applied to the exciter 34. The signals applied to the exciter 34 are in the form of pulses having a frequency and amplitude which induces excitations in the anelastic stress range of the tested object 30.

To detect the excitations induced in the tested object 30, a detector 42 is located near or in contact with the object 30 at a location other than that where the exciting pulse is applied. As with the exciter 34, a number of different devices can be used for the detector 42. For example, the detector 42 can be in the form of an accelerometer which is sensitive to movement of the object 30. Alternatively, magnetic or capacitance type pick-up devices which are also sensitive to movement of the object induced by vibrator excitations can be used. Where an acoustic transmitter 36 is used as the exciter, it is preferable to use an acoustic pick-up device 44 (FIG. 4), such as a microphone, for detecting the audio frequency excitations.

The output signal of the detector 42 can be amplified by a suitable amplifier, such as a cathode follower 46. The amplified signal can be fed into a frequency analyzer 48 to discriminate out undesirable signals. For example, in addition to the induced excitations, the detector 42 may pick up movement of the object due to air currents, noise, or the like. The frequency analyzer 48 serves to block these signals and pass only the signal produced by the induced excitation.

The output signal of the frequency analyzer may be fed into an oscilloscope 50 for display of the signal. From this display, an operator can use the results to make the necessary calculations and record the measured specific damping capacity of the object, in accordance with the description of FIG. 2.

A modified embodiment of the apparatus for measuring the specific damping capacity of a tested object 30 is illustrated in FIG. 4. In this embodiment, pulses of the output signal of the beat frequency oscillator 38 are passed to the exciter 36 by means of a signal gating system 52. The gating system 52 also sends triggering information to a storage oscilloscope 54. Among other functions, the storage oscilloscope 54 can measure the time delay between transmission of the exciting signal by the exciter 36 and receipt of the excitation at the detector 44.

A counter 56 records the number of pulses in the output signal of the beat frequency oscillator 36. This counter can be used among other things, to monitor the number of pulses applied during the testing of the object, and hence the duration of the test.

In addition to the storage oscilloscope 54, a level recorder 58 can be used to display the output signal from the frequency analyzer 48. This provides a hard copy display which enables calculation of the specific damping capacity to be more readily performed.

In a further modified embodiment of the invention, a microprocessor unit 60 can be incorporated with the measuring apparatus to automatically compute the specific damping capacity. The microprocessor unit may include a digitizer 62 for receiving and converting the amplitude of the pulses in the output signal from the frequency analyzer 48 to digital pulses. The received signals are conditioned or otherwise suitably processed in a microprocessor 64.

To derive the specific damping capacity from the received signals, the microprocessor unit 64 can be programmed to calculate the slope of the line 10 (FIGS. 1a and 1b) from the differences between successive amplitude signals. This calculation, determinative of the specific damping capacity, can then be displayed on a print out 72 to be recorded.

The microprocessor unit 60 might also have a memory unit incorporated therein to store the calculated values for the specific damping capacity. The processor 64 can be programmed to compute the baseline 14 and the predicted limit values 18, 20 from the calculated values for the specific damping capacity. In such a case the display on the print out 72 would be in the form of the graph illustrated in FIG. 2.

The location of various input and output signals for testing an in situ object is illustrated in FIG. 5. The structure illustrated generally is an ocean simulating facility chamber 74. Such a structure is subject to very high fluid pressures and must be regularly tested to determine its structural soundness. The various solid lines 76, 78 within the structure indicate the location of a weld between two adjoining components.

Excitation input signals are applied to the structure at a plurality of points 77A-77J. The amplitude of the various input signals are detected at a plurality of associated detection points 79A-79J. The output signal from the beat frequency oscillator 38 could be commutated to be successively delivered to an exciter located at each of the nine input locations. Likewise, the output signals from the ten detectors could be multiplexed or otherwise successively fed into the frequency analyzer 48.

The detectors positioned at output locations 79B and 79C detect the same input signal. The location of an incipient flaw can be detected with a reasonable degree of accuracy by utilizing a plurality of detectors. The detector whose output signal shows the greatest change in specific damping capacity will indicate generally the location of the flaw. The flaw is most likely to be located on or near a line directly connecting the location of the input signal and the detector of interest.

The previously described technique provides a highly useful method for detecting incipient flaws and predicting useful life of an object. In one application thereof, a notch 80 was placed in a ring 30 such as that illustrated in FIG. 3. Cyclic loading was applied to the ring 30 and periodically interrupted to measure the specific damping capacity. The notch 80 was examined after each measurement for crack detection.

A crack was detected in the notch after 15,000 load cycles. However, a significant change in the specific damping capacity was noticed after 7,000 cycles. From this it can be seen that detection of a flaw occurs early enough in the life of the object to provide useful life information as well as an opportunity to moderate the flaw and take corrective procedures before damage occurs.

It will be obvious to those of ordinary skill in the art that other embodiments come within the spirit and essential characteristics of the present invention. The presently disclosed embodiments are therefore to be considered in all respects as illustrative and not restrictive. The scope of the invention is defined by the appended claims rather than the foregoing description, and all changes which come within the meaning and range of equivalency of the claims are expressly intended to be embraced therein.

What is claimed is:

1. A method for detecting an incipient flaw in an object by measurement of the specific damping capacity of the object, comprising the steps of:
   inducing an excitation having a predetermined amount of energy in the object to produce a stress in the anelastic stress range;
   measuring a value indicative of changes in the specific damping capacity occurring in the object;
   recording the measured value;
   periodically repeating the steps of inducing, measuring and recording;
   determining from the recorded values a baseline for the specific damping capacity of the object;
   establishing a set of predetermined values which indicates the expected relationship of said measured values to said baseline; and
   thereafter checking at intervals for a difference which is greater than a predetermined amount between the recorded values and the predetermined values.

2. The method of claim 1 wherein said inducing step includes applying a pulse having a predetermined amplitude to a first location on the object and said measuring step includes measuring the amplitude of said pulse at a location on the object other than said first location.

3. The method of claim 2 wherein said measuring step includes measuring the amplitude of said pulse at a plurality of locations on the object.

4. The method of claim 3 further including the step of determining the location of a flaw in the object from the plurality of measurements made.

5. The method of claim 2 wherein said inducing step includes applying a plurality of said pulses at a single frequency other than the resonant frequency of the object.

6. The method of claim 1 further including the step of determining the expected utility life of the object from any differences greater than said predetermined amount which are observed.

7. An in-situ method of non-destructive determination of the specific damping capacity of an object comprising the steps of:
   inducing an excitation in an in-situ object by applying a series of pulses to a point on the object at a predetermined frequency, the amplitude of said pulses being such that stresses in the anelastic stress range are produced;
   measuring the amplitude of the pulses at a point on the object; and
   determining the logarithmic decrement from the amplitude of the measured pulses in the in-situ object.

8. The method of claim 7 further including the steps of:
   repeating the steps of inducing, measuring and determining;
   recording each determined value; and
   detecting whether an incipient flaw is present in the in-situ object by checking for an unexpected difference between the magnitudes of sequentially calculated values.

9. Apparatus for non-destructive evaluation of the specific damping capacity of an in-situ object comprising:
   means for inducing an excitation having a predetermined amount of energy in an in-situ object to produce a stress in the anelastic stress range;
   means for measuring the changes in the specific damping capacity occurring in the in-situ object; and
   means for recording said measured changes.

10. The apparatus of claim 9 wherein said inducing means includes an exciting means and means for driving said exciting means.

11. The apparatus of claim 10 wherein said exciting means is a magnetic exciter adapted for physical connection with the object.

12. The apparatus of claim 10 wherein said exciting means is an acoustic transmitter adapted to be acoustically coupled with the object.

13. The apparatus of claim 10 wherein said driving means includes a beat frequency oscillator for generating a series of pulses at a single predetermined frequency and gating means for transmitting at least some of the pulses generated by said oscillator to said exciting means.

14. The apparatus of claim 13 wherein said gating means includes a tone burst generator.

15. The apparatus of claim 9 wherein said inducing means includes means for applying a pulse having a predetermined amplitude to a first location on the object and said percentage measuring means includes means for measuring the amplitude of said pulse at a location on the object other than said first location.

16. The apparatus of claim 15 wherein said amplitude measuring means includes an accelerometer.

17. The apparatus of claim 15 wherein said amplitude measuring means includes an acoustic pickup device adapted to be acoustically coupled with the object.

18. The apparatus of claim 15 wherein said amplitude measuring means includes a frequency analyzer.

19. The apparatus of claim 15 further including means for determining said percentage of decay from the measured amplitude of said pulse.

20. The apparatus of claim 19 further including means for determining a baseline specific damping capacity for said object.

21. The apparatus of claim 20 further including means for determining the normal expected difference between a determined percentage value and said baseline.

22. The apparatus of claim 21 further including means for indicating when a determined percentage value differs from the expected difference by more than a predetermined amount.

23. The apparatus of claim 9 further including means for displaying said percentage of energy decay.

* * * * *